United States Patent
Tsuchida

(10) Patent No.: US 8,207,259 B2
(45) Date of Patent: Jun. 26, 2012

(54) POLYFUNCTIONAL EPOXY-CONTAINING ORGANOSILICON COMPOUND, MAKING METHOD, COATING COMPOSITION, AND COATED ARTICLE

(75) Inventor: Kazuhiro Tsuchida, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 322 days.

(21) Appl. No.: 12/437,937

(22) Filed: May 8, 2009

(65) Prior Publication Data

US 2009/0286924 A1    Nov. 19, 2009

(30) Foreign Application Priority Data

May 16, 2008   (JP) .................................. 2008-129488

(51) Int. Cl.
  *C08L 83/00* (2006.01)
  *C08L 63/00* (2006.01)
  *C08G 77/00* (2006.01)
(52) U.S. Cl. ........... 524/588; 523/400; 523/402; 528/27
(58) Field of Classification Search .................... 523/400
  See application file for complete search history.

(56) References Cited

U.S. PATENT DOCUMENTS

| 5,336,786 A | 8/1994 | Shiobara et al. |
| 6,426,148 B1 * | 7/2002 | Barsotti et al. ............. 428/423.1 |
| 2006/0003165 A1 * | 1/2006 | Akatsuka et al. ............ 428/413 |
| 2008/0221238 A1 * | 9/2008 | Su et al. ....................... 523/435 |

FOREIGN PATENT DOCUMENTS

| GB | 834326 | 5/1960 |
| JP | 6-172370 A | 6/1994 |
| WO | 2008-112150 A1 | 9/2008 |

OTHER PUBLICATIONS

European Search Report dated Sep. 3, 2009, issued in corresponding European Patent Application No. 09159978.7.

\* cited by examiner

*Primary Examiner* — Mark Eashoo
*Assistant Examiner* — David Karst
(74) *Attorney, Agent, or Firm* — Westerman, Hattori, Daniels & Adrian, LLP

(57) ABSTRACT

A polyglycidyl ether compound having a plurality of epoxy groups and a hydroxy group in the molecule is reacted with a silane coupling agent having an isocyanate group, and specifically the hydroxyl group on the polyglycidyl ether compound is reacted with the isocyanate group on the silane coupling agent. Then an organosilicon compound having a plurality of epoxy groups per alkoxysilyl group is synthesized wherein the ratio of epoxy groups to alkoxysilyl groups may be adjusted as desired. The resulting organosilicon compound is useful as a primer and resin modifier.

3 Claims, 2 Drawing Sheets

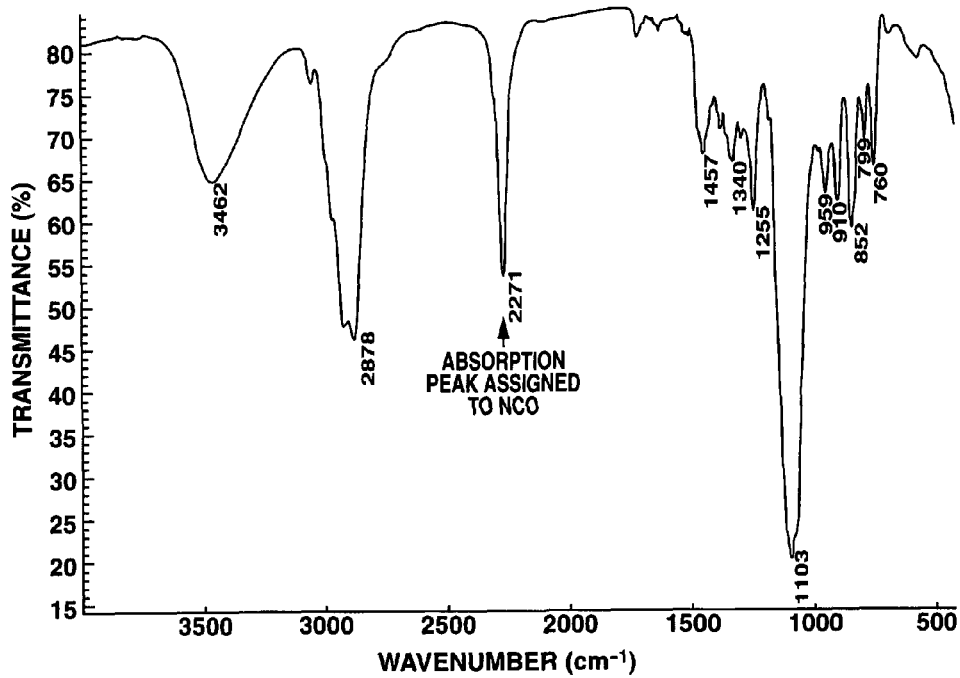
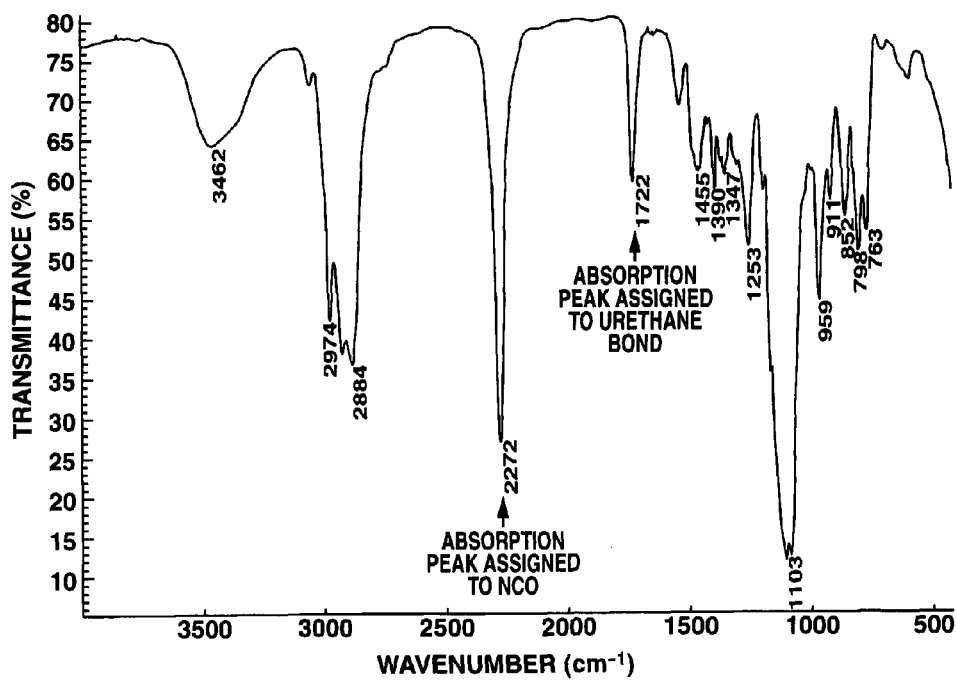

POLYFUNCTIONAL EPOXY-CONTAINING ORGANOSILICON COMPOUND, MAKING METHOD, COATING COMPOSITION, AND COATED ARTICLE

CROSS-REFERENCE TO RELATED APPLICATION

This non-provisional application claims priority under 35 U.S.C. §119(a) on Patent Application No. 2008-129488 filed in Japan on May 16, 2008, the entire contents of which are hereby incorporated by reference.

TECHNICAL FIELD

This invention relates to novel polyfunctional epoxy-containing organosilicon compounds useful as epoxy silane coupling agents, and a method for preparing the same. More particularly, it relates to polyfunctional epoxy-containing organosilicon compounds having a plurality of epoxy groups and hydrolyzable silyl groups, which are water-soluble and fully reactive with organic resins and inorganic materials, and a method for preparing the same. It also relates to coating compositions comprising the organosilicon compounds and articles coated therewith.

BACKGROUND ART

Silane coupling agents are compounds including both a moiety which is reactive with inorganic matter and another moiety which is fully reactive with and soluble in organic matter, within their molecule. Since they serve as adhesive aids at the interface between inorganic and organic materials, they are widely employed as a composite resin modifier. The majority of silane coupling agents and partial hydrolytic condensates thereof, often referred to as siloxane oligomers, are compounds containing at least two alkoxysilyl groups per organic functional group, whereas only a few compounds having at least two organic functional groups per alkoxysilyl group are available.

One exemplary organic compound containing at least two epoxy groups per alkoxysilyl group is disclosed in JP-A 06-172370, which relates to an organic compound having two glycidoxy groups and a trimethoxysilylpropyl group attached to an aromatic ring. Because of its structure, this compound can be endowed with only two epoxy groups per alkoxysilyl group. It is impossible from the molecular design aspect to incorporate more epoxy groups therein.

Citation List
Patent Document 1: JP-A H06-172370

SUMMARY OF INVENTION

An object of the invention is to provide polyfunctional epoxy-containing organosilicon compounds having a plurality of epoxy groups capable of reacting with an organic resin portion to form bonds therewith, and useful as a primer or resin modifier; a method for preparing the compounds, a coating composition comprising the compounds, and an article coated therewith.

The inventors have succeeded in synthesizing an organosilicon compound having a plurality of epoxy groups per alkoxysilyl group by combining a polyglycidyl ether compound having a plurality of epoxy groups and a hydroxy group in the molecule with a silane coupling agent having an isocyanate group such that the hydroxyl group on the polyglycidyl ether compound may react with the isocyanate group on the silane coupling agent. In the organosilicon compound, the ratio of epoxy groups to alkoxysilyl groups may be adjusted as desired.

In a first aspect, the invention provides a polyfunctional epoxy-containing organosilicon compound having the general formula (1):

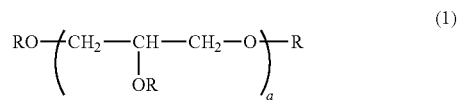

wherein R is each independently selected from the group consisting of hydrogen, glycidyl and alkoxysilyl of the formula (2):

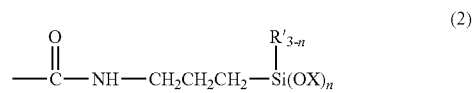

wherein R' is $C_1$-$C_6$ alkyl, X is hydrogen or $C_1$-$C_4$ alkyl, n is an integer of 1 to 3, at least one R being alkoxysilyl and at least two R's being glycidyl, and "a" is a number from 1 to 100.

In a second aspect, the invention provides a polyfunctional epoxy-containing organosilicon compound having the general formula (3):

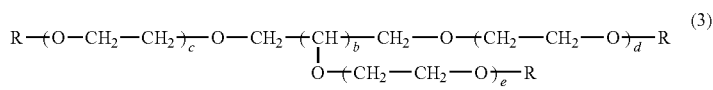

wherein R is as defined above, b is a number from 4 to 10, c is a number from 0 to 10, d is a number from 0 to 10, and e is a number from 0 to 10.

In a third aspect, the invention provides a method for preparing a polyfunctional epoxy-containing organosilicon compound having at least two epoxy groups and at least one alkoxysilyl group in the molecule, comprising the step of combining a compound having at least two epoxy groups and at least one hydroxy group in the molecule with a silane coupling agent having an isocyanate group and at least one alkoxy group such that the isocyanate group reacts with the hydroxyl group.

In one preferred embodiment, the compound having at least two epoxy groups and at least one hydroxy group in the molecule is a (poly)glycerin polyglycidyl ether, and the resulting polyfunctional epoxy-containing organosilicon compound is a polyfunctional epoxy-containing organosilicon compound of formula (1). In another preferred embodiment, the compound having at least two epoxy groups and at least one hydroxy group in the molecule is a sorbitol polyglycidyl ether, and the resulting polyfunctional epoxy-containing organosilicon compound is a polyfunctional epoxy-containing organosilicon compound of formula (3).

In a fourth aspect, the invention provides a coating composition comprising the polyfunctional epoxy-containing organosilicon compound of formula (1) or (3) and water and/or an organic solvent.

An article coated with the coating composition is also contemplated herein.

ADVANTAGEOUS EFFECTS OF INVENTION

The polyfunctional epoxy-containing organosilicon compound has a plurality of epoxy groups per hydrolyzable silyl group in the molecule, offers an increased number of reactive sites with an organic resin, as compared with conventional epoxy silane coupling agents, thus achieves an enhanced bond strength to the organic resin. When glass fibers, silica and other inorganic fillers, ceramics, and metal substrates are coated and treated with the polyfunctional epoxy-containing organosilicon compound, significant adhesion improvements are achieved as compared with the conventional epoxy silane coupling agents containing epoxy and silyl groups in a 1:1 ratio within the molecule.

BRIEF DESCRIPTION OF DRAWINGS

FIG. 1 is a diagram showing an IR spectrum of a reactant prior to reaction in Example 1.

FIG. 2 is a diagram showing an IR spectrum of an intermediate in Example 1.

DESCRIPTION OF EMBODIMENTS

Figure 3:
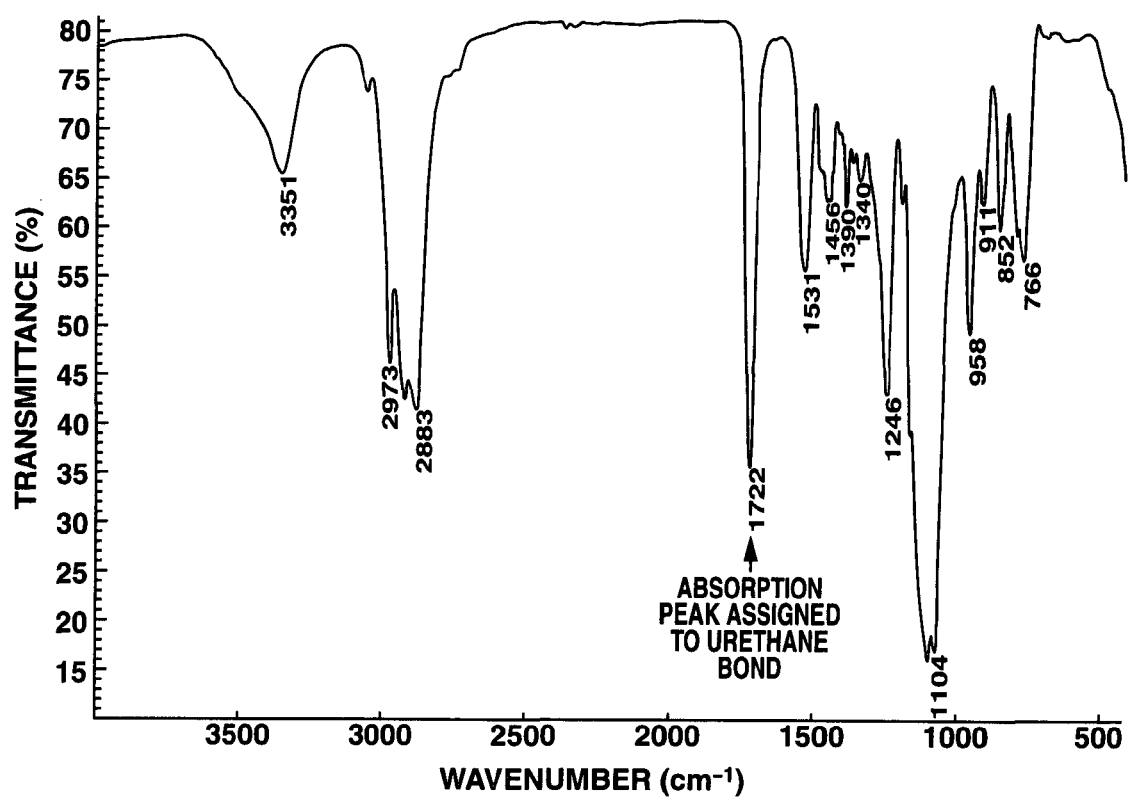
FIG. 3 is a diagram showing an IR spectrum of a compound at the end of reaction in Example 1.

As used herein, the notation (Cn-Cm) means a group containing from n to m carbon atoms per group.

The first aspect of the invention provides a polyfunctional epoxy-containing organosilicon compound having the general formula (1):

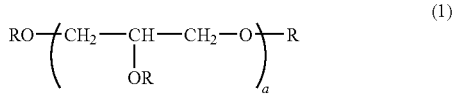

wherein R is each independently selected from among hydrogen, a glycidyl group and an alkoxysilyl group of the formula (2):

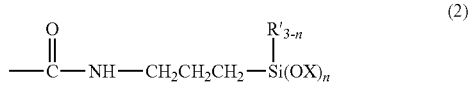

(wherein R' is $C_1$-$C_6$ alkyl, X is hydrogen or $C_1$-$C_4$ alkyl, n is an integer of 1 to 3), at least one R being alkoxysilyl and at least two R's being glycidyl, and "a" is a number from 1 to 100 (i.e., $1 \leq a \leq 100$).

The second aspect of the invention provides a polyfunctional epoxy-containing organosilicon compound having the general formula (3):

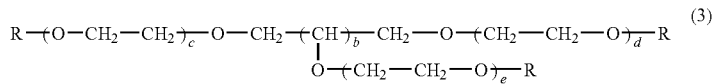

wherein R is each independently selected from among hydrogen, a glycidyl group and an alkoxysilyl group of the formula (2):

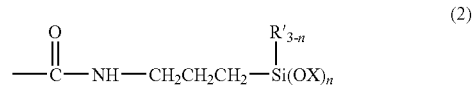

(wherein R' is $C_1$-$C_6$ alkyl, X is hydrogen or $C_1$-$C_4$ alkyl, n is an integer of 1 to 3), at least one R being alkoxysilyl and at least two R's being glycidyl, b is a number from 4 to 10, c is a number from 0 to 10, d is a number from 0 to 10, and e is a number from 0 to 10.

The subscripts "a" to "e" are preferably numbers in the range: $1 \leq a \leq 40$, $4 \leq b \leq 8$, $0 \leq c \leq 8$, $0 \leq d \leq 8$, and $0 \leq e \leq 8$; and more preferably $1 \leq a \leq 30$, $4 \leq b \leq 5$, $0 \leq c \leq 5$, $0 \leq d \leq 5$, and $0 \leq e \leq 5$.

As noted above, "a" is at least 1. The compounds of formula (1) wherein a=1 are glycerin derivatives, although preference is given to polyglycerin derivatives of formula (1) wherein "a" is at least 2, more preferably at least 3, even more preferably at least 4, for example, diglycerin derivatives of a=2 and triglycerin derivatives of a=3 because an increased number of reactive sites are available. In formula (3), each of "c" to "e" is equal to or more than 0, and the sum c+d+e is preferably 0 to 25, and more preferably 3 to 20.

In the compound of formula (1), a functional group ratio of glycidyl groups (A) to alkoxysilyl groups (B) on a molar basis is preferably in the range: $0.02 \leq A/B \leq 100$, more preferably $0.05 \leq A/B \leq 50$, and even more preferably $0.1 \leq A/B \leq 10$. In case of A/B<0.02, alkoxysilyl groups are in excess, such a design structure is difficult to synthesize, and products, if obtained, are less stable. In case of A/B>100, few alkoxysilyl groups are contained, and little of the alkoxysilyl effect is developed.

In the compound of formula (3), a functional group ratio of glycidyl groups (C) to alkoxysilyl groups (D) on a molar basis is preferably in the range: $0.1 \leq C/D \leq 9$, and more preferably $0.2 \leq C/D \leq 5$.

In the polyfunctional epoxy-containing organosilicon compound, some hydroxyl groups in the structure of a polyglycidyl ether compound having a plurality of epoxy groups have reacted with a silane coupling agent to form bonds. Specifically, a silane coupling agent having an isocyanate group (referred to as "isocyanatosilane") is used, and thus a urethane bond forms between hydroxyl and isocyanate.

In another aspect of the invention, a polyfunctional epoxy-containing organosilicon compound is prepared by combining a polyglycidyl ether compound having at least two epoxy groups and at least one hydroxy group in the molecule with a silane coupling agent having an isocyanate group and at least one alkoxy group such that the isocyanate group on the coupling agent reacts with the hydroxyl group on the ether compound, thus yielding a polyfunctional epoxy-containing organosilicon compound having at least two epoxy groups and at least one alkoxysilyl group in the molecule.

In preferred embodiments of the method, a (poly)glycerin polyglycidyl ether is used as the polyglycidyl ether compound having at least two epoxy groups and at least one hydroxy group in the molecule, then an organosilicon compound of formula (1) is obtained; and a sorbitol polyglycidyl ether is used as the polyglycidyl ether compound having at least two epoxy groups and at least one hydroxy group in the molecule, then an organosilicon compound of formula (3) is obtained.

The (poly)glycerin polyglycidyl ether used herein typically has the general formula (4):

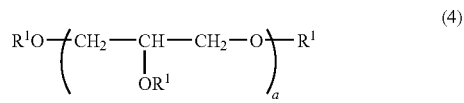

wherein $R^1$ is hydrogen or glycidyl, at least one $R^1$ being hydrogen and at least two $R^1$'s being glycidyl, and "a" is as defined above. A ratio of glycidyl groups (E) to hydroxyl groups (F) on a molar basis is preferably in the range: $0.01 \leq E/F \leq 100$, more preferably $0.02 \leq E/F \leq 50$, and even more preferably $0.1 \leq E/F \leq 40$. Also preferably the (poly) glycerin polyglycidyl ether has an epoxy equivalent of 100 to 500, more preferably 100 to 400, and even more preferably 100 to 300. An ether with too low an epoxy equivalent may be difficult to prepare whereas too high an epoxy equivalent corresponds to so low an epoxy content that a polyfunctional epoxy-containing organosilicon compound obtained therefrom may have unsatisfactory properties.

The sorbitol polyglycidyl ether used herein typically has the general formula (5):

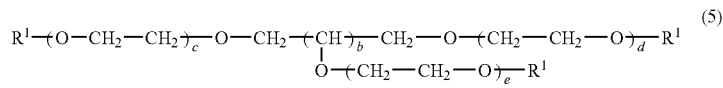

wherein $R^1$ is hydrogen or glycidyl, at least one $R^1$ being hydrogen and at least two $R^1$'s being glycidyl, and "b" to "e" are as defined above. A ratio of glycidyl groups (G) to hydroxyl groups (H) on a molar basis is preferably in the range: $0.1 \leq G/H \leq 9$, and more preferably $0.2 \leq G/H \leq 5$. Also preferably the sorbitol polyglycidyl ether has an epoxy equivalent of 100 to 500, more preferably 100 to 400, and even more preferably 100 to 300. An ether with too low an epoxy equivalent may be difficult to prepare whereas too high an epoxy equivalent corresponds to so low an epoxy content that a polyfunctional epoxy-containing organosilicon compound obtained therefrom may have unsatisfactory properties.

These polyglycidyl ether compounds are commercially available. For example, the (poly)glycerin polyglycidyl ether is available under the trade name of SR-4GL from Sakamoto Yakuhin Kogyo Co., Ltd. and Denacol EX-1310, EX-1410 and EX-1610 from Nagase ChemteX Corp. The sorbitol polyglycidyl ether is available under the trade name of Denacol EX-610U from Nagase ChemteX Corp.

Any silane coupling agent having a functional group which is non-reactive with an epoxy group, but selectively reactive with a hydroxyl group may be used for introducing hydrolyzable silyl groups. Inter alia, isocyanatosilanes are preferred.

Illustrative examples of the isocyanatosilane include 3-isocyanatopropyltrimethoxysilane, 3-isocyanatopropylmethyldimethoxysilane, 3-isocyanatopropyldimethylmethoxysilane, 3-isocyanatopropyltriethoxysilane, 3-isocyanatopropylmethyldiethoxysilane, and 3-isocyanatopropyldimethylethoxysilane. Inter alia, 3-isocyanatopropyltriethoxysilane and 3-isocyanatopropyltrimethoxysilane are preferred.

Preferably the polyglycidyl ether compound and the isocyanatosilane are combined in such a ratio that 0.01 to 1 mole, especially 0.1 to 1 mole of isocyanate groups on the isocyanatosilane are available per mole of hydroxyl groups on the polyglycidyl ether compound.

While the polyfunctional epoxy-containing organosilicon compound is obtainable through reaction of the polyglycidyl ether compound with the isocyanatosilane, the reaction temperature is preferably in the range of 25 to 90° C., and more preferably 40 to 80° C. At temperatures below 25° C., reaction may proceed at a lower rate. At temperatures above 90° C., side reactions may occur, typically ester exchange may occur between hydroxyl groups on the polyglycidyl ether and alkoxysilyl sites on the isocyanatosilane to form an alcohol. The reaction time is generally 10 minutes to 24 hours, but not limited thereto.

Upon reaction of the polyglycidyl ether compound with the isocyanatosilane, any solvent which is inert to isocyanate groups may be used. Suitable solvents include hydrocarbon solvents, aromatic solvents, ketone solvents, amide solvents, ester solvents, and ether solvents. Specifically, exemplary hydrocarbon solvents include pentane, hexane, heptane, octane, decane, and cyclohexane; exemplary aromatic solvents include benzene, toluene, and xylene; exemplary ketone solvents include acetone, methyl ethyl ketone, methyl isobutyl ketone, and cyclohexanone; exemplary amide solvents include formamide, dimethylformamide, pyrrolidone, and N-methylpyrrolidone; exemplary ester solvents include ethyl acetate, butyl acetate, and lactone; and exemplary ether solvents include diethyl ether, dibutyl ether, cyclopentyl methyl ether, tetrahydrofuran, and 1,4-dioxane.

Upon reaction of the polyglycidyl ether compound with the isocyanatosilane, a catalyst may be used for increasing the reaction rate. Those catalysts which are generally used in urethane reaction may be used, for example, dibutyltin oxide, dioctyltin oxide, and tin(II) bis(2-ethylhexanoate). The catalyst is used in a catalytic amount, and specifically 0.001 to 1% by weight based on the total weight of the polyglycidyl ether compound and isocyanatosilane.

The polyfunctional epoxy-containing organosilicon compound thus obtained should preferably have a weight average molecular weight (Mw) of 200 to 10,000, and more preferably 300 to 8,000, as measured by gel permeation chromatography (GPC) versus polystyrene standards. A compound with too low Mw may be difficult to prepare whereas a compound with too high Mw may interfere with working.

A further aspect of the invention is a coating composition comprising the polyfunctional epoxy-containing organosilicon compound as a primary component and a solvent. The solvent used herein is not particularly limited as long as the organosilicon compound may be dissolved therein. From the standpoints of safety, solubility and volatility, water and alcohols are preferred. Of the alcohols, methanol and ethanol are most preferred. It is acceptable to use water, alcohols and other solvents which are reactive with isocyanate groups because the isocyanate groups have been reacted at this point.

The coating composition is preferably prepared such that the polyfunctional epoxy-containing organosilicon compound is present in an amount of 5 to 90% by weight, and more preferably 10 to 80% by weight of the overall composition, the balance being the solvent.

The coating composition is applicable to various substrates. The substrates which may be coated and treated with the polyfunctional epoxy-containing organosilicon compound include inorganic materials which will react with hydrolyzable silyl groups to form bonds and organic resins which will react with epoxy groups to form bonds while their shape is not particularly limited. Typical inorganic materials include inorganic fillers such as (hollow) silica, titania, zirconia, and alumina, glass fibers and glass fiber articles such as glass cloth, glass tape, glass mat, and glass paper, ceramics, and metals. Typical organic resins include epoxy resins, phenolic resins, polyimide resins, and unsaturated polyester resins.

EXAMPLE

Examples of the invention are given below by way of illustration and not by way of limitation. In Examples, the viscosity is measured at 25° C. by a Brookfield rotational viscometer. Mw is a weight average molecular weight as measured by gel permeation chromatography (GPC) versus polystyrene standards. The epoxy equivalent (in g/mol) is a mass of an epoxy compound to provide 1 mole of epoxy group.

Example 1

A 1-L separable flask equipped with a stirrer, reflux condenser, dropping funnel and thermometer was charged with 100 g of polyglycerin polyglycidyl ether having an epoxy equivalent of 168 (SR-4GL, Sakamoto Yakuhin Kogyo Co., Ltd.) and heated at 80° C. To the flask, 49.0 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 1,800, a viscosity of 1,074 mPa-s, and an epoxy equivalent of 265. It is a compound of formula (1) wherein "a" is 9 on average and a ratio A/B=3. FIG. 1 is an IR spectrum of the reactant prior to reaction, FIG. 2 is an IR spectrum of an intermediate during the reaction process, and FIG. 3 is an IR spectrum of the compound at the end of reaction.

Example 2

A 1-L separable flask equipped with a stirrer, reflux condenser, dropping funnel and thermometer was charged with 100 g of polyglycerin polyglycidyl ether having an epoxy equivalent of 168 (SR-4GL, Sakamoto Yakuhin Kogyo Co., Ltd.) and 0.6 g of dioctyltin oxide and heated at 80° C. To the flask, 49.0 g of 3-isocyanatopropyltriethoxysilane was added dropwise. The contents were heated and stirred at 80° C. for 2 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 1,800, a viscosity of 1,014 mPa-s, and an epoxy equivalent of 267. It is a compound of formula (1) wherein "a" is 9 on average and a ratio A/B=3.

Example 3

A 1-L separable flask equipped with a stirrer, reflux condenser, dropping funnel and thermometer was charged with 100 g of polyglycerin polyglycidyl ether having an epoxy equivalent of 168 (SR-4GL, Sakamoto Yakuhin Kogyo Co., Ltd.) and heated at 80° C. To the flask, 24.5 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 1,700, a viscosity of 1,184 mPa-s, and an epoxy equivalent of 219. It is a compound of formula (1) wherein "a" is 9 on average and a ratio A/B=6.

Example 4

A 1-L separable flask equipped with a stirrer, reflux condenser, dropping funnel and thermometer was charged with 100 g of polyglycerin polyglycidyl ether having an epoxy equivalent of 168 (SR-4GL, Sakamoto Yakuhin Kogyo Co., Ltd.) and heated at 80° C. To the flask, 441.0 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 2,500, a viscosity of 1,374 mPa-s, and an epoxy equivalent of 910. It is a compound of formula (1) wherein "a" is 9 on average and a ratio A/B=0.3.

Example 5

A 1-L separable flask equipped with a stirrer, reflux condenser, dropping funnel and thermometer was charged with 100 g of polyglycerin polyglycidyl ether having an epoxy equivalent of 172 (Denacol EX-1310, Nagase ChemteX Corp.) and heated at 80° C. To the flask, 49.7 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 1,870, a viscosity of 108 mPa-s, and an epoxy equivalent of 259. It is a compound of formula (1) wherein "a" is 7 on average and a ratio A/B=3.

Example 6

A 1-L separable flask equipped with a stirrer, reflux condenser, dropping funnel and thermometer was charged with 100 g of polyglycerin polyglycidyl ether having an epoxy equivalent of 172 (Denacol EX-1410, Nagase ChemteX Corp.) and heated at 80° C. To the flask, 52.2 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 1,700, a viscosity of 200 mPa-s, and an epoxy equivalent of 247. It is a compound of formula (1) wherein "a" is 7 on average and a ratio A/B=3.

Example 7

A 1-L separable flask equipped with a stirrer, reflux condenser, dropping funnel and thermometer was charged with 100 g of polyglycerin polyglycidyl ether having an epoxy equivalent of 172 (Denacol EX-1610, Nagase ChemteX Corp.) and heated at 80° C. To the flask, 49.9 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow liquid having a Mw of 3,800, a viscosity of 1,421 mPa-s, and an epoxy equivalent of 261. It is a compound of formula (1) wherein "a" is 16 on average and a ratio A/B=3.

Example 8

A 1-L separable flask equipped with a stirrer, reflux condenser, dropping funnel and thermometer was charged with 100 g of sorbitol polyglycidyl ether having an epoxy equivalent of 220 (Denacol EX-610U, Nagase ChemteX Corp.) and heated at 80° C. To the flask, 39.8 g of 3-isocyanatopropyltriethoxysilane was added dropwise. The contents were heated and stirred at 80° C. for 4 hours while the reaction process was monitored by IR spectroscopy. The completion of reaction was identified when the absorption peak assigned to an isocyanate group in the reactant disappeared and the absorption peak assigned to a urethane bond was observed instead. The reaction product was a pale yellow cloudy liquid having a Mw of 3,600, a viscosity of 1,114 mPa-s, and an epoxy equivalent of 315. It is a compound of formula (3) wherein b=4 and c=d=e=2, and a ratio C/D=3.

Preparation of Coating Composition

Coating compositions were prepared by dissolving the polyfunctional epoxy-containing organosilicon compounds obtained in Examples 1 to 8 and γ-glycidoxypropyltriethoxysilane (KBE-403 by Shin-Etsu Chemical Co., Ltd.) as a comparative example in methanol in an active component concentration of 10 wt %. They were used as a primer in an adhesion test to be described below.

Preparation of Polyurethane Elastomer

With stirring, 150 parts by weight of polyoxytetramethylene glycol having a number average molecular weight of 1,000 was mixed with 100 parts by weight of 1,6-xylene glycol, 0.5 part by weight of water, 200 parts by weight of hexamethylene diisocyanate, and 800 parts by weight of dimethylformamide. The mixture was heated at 90° C. and stirred at the temperature for 2 hours for reaction. To the reaction mixture, 3 parts by weight of dibutylamine was added to quench the reaction. The excess of amine was neutralized with acetic anhydride. In this way, a polyurethane elastomer was obtained.

Adhesion Test

To glass, iron and aluminum plates, each of the coating compositions (primers) was brush coated and dried at 120° C. for 5 minutes. The polyurethane elastomer was brush coated thereon and dried at 100° C. for 10 minutes. The polyurethane coating was scribed in orthogonal directions at intervals of 1 mm to define 100 square sections. Adhesive (Cellophane®) tape was pressure attached to the coating and then peeled. The number of peeled sections was counted, based on which the enhancement by primer of adhesion between urethane resin and inorganic substrate was evaluated. The results of the adhesion test including Examples and Comparative Example are shown in Tables 1 to 3.

TABLE 1

| Substrate | Primer active component | Adhesion test |
|---|---|---|
| Glass plate | Example 1 | 100/100 |
| | Example 2 | 100/100 |
| | Example 3 | 100/100 |
| | Example 4 | 100/100 |
| | Example 5 | 100/100 |
| | Example 6 | 100/100 |
| | Example 7 | 100/100 |
| | Example 8 | 100/100 |
| | Comparative Example | 60/100 |

TABLE 2

| Substrate | Primer active component | Adhesion test |
|---|---|---|
| Iron plate | Example 1 | 100/100 |
| | Example 2 | 100/100 |
| | Example 3 | 100/100 |
| | Example 4 | 100/100 |
| | Example 5 | 100/100 |
| | Example 6 | 100/100 |
| | Example 7 | 100/100 |
| | Example 8 | 100/100 |
| | Comparative Example | 40/100 |

TABLE 3

| Substrate | Primer active component | Adhesion test |
|---|---|---|
| Aluminum plate | Example 1 | 100/100 |
| | Example 2 | 100/100 |
| | Example 3 | 100/100 |
| | Example 4 | 100/100 |
| | Example 5 | 100/100 |
| | Example 6 | 100/100 |
| | Example 7 | 100/100 |
| | Example 8 | 100/100 |
| | Comparative Example | 40/100 |

For the primers of Examples, the number of peeled sections was zero (0) on any of the substrates, indicating excellent adhesion enhancement.

The foregoing Examples demonstrate that the polyfunctional epoxy-containing organosilicon compounds of the invention are effective in enhancing the bond at the organic/inorganic material interface.

Japanese Patent Application No. 2008-129488 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polyfunctional epoxy-containing organosilicon compound having the general formula (3):

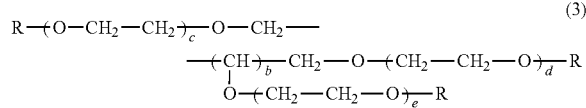

wherein R is each independently selected from the group consisting of hydrogen, glycidyl and alkoxysilyl of the formula (2):

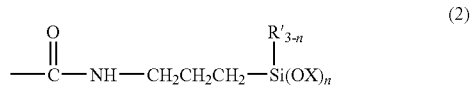

wherein in formula (2), R' is $C_1$-$C_6$ alkyl, X is hydrogen or $C_1$-$C_4$ alkyl, n is an integer of 1 to 3, wherein in formula (3), at least one R is alkoxysilyl and at least two Rs are glycidyl, b is a number from 4 to 10, c is a number from 0 to 10, d is a number from 0 to 10, and e is a number from 0 to 10, and the sum c+d+e is 3 to 20.

2. A coating composition comprising the polyfunctional epoxy-containing organosilicon compound of claim 1 and water and/or an organic solvent.

3. An article coated with the coating composition of claim 1.

* * * * *